(12) United States Patent
Younker et al.

(10) Patent No.: US 8,834,355 B2
(45) Date of Patent: Sep. 16, 2014

(54) DELIVERY DEVICE

(75) Inventors: Marlin E. Younker, Lantana, FL (US); Dean J. Secrest, Concord, OH (US); Robert M. Stuba, Macedonia, OH (US); Christopher J. Kaye, Concord, OH (US); K. Randall John, Chardon, OH (US); William Ross Mancini, Eastlake, OH (US)

(73) Assignee: U.S. Endoscopy Group, Inc., Mentor, OH (US)

( * ) Notice: Subject to any disclaimer, the term of this patent is extended or adjusted under 35 U.S.C. 154(b) by 1763 days.

(21) Appl. No.: 11/137,525

(22) Filed: May 25, 2005

(65) Prior Publication Data

US 2005/0267361 A1 Dec. 1, 2005

Related U.S. Application Data

(60) Provisional application No. 60/574,070, filed on May 25, 2004.

(51) Int. Cl.
  *A61B 1/00* (2006.01)
  *A61B 1/04* (2006.01)
  *A61B 5/07* (2006.01)
  *A61M 25/01* (2006.01)
  *A61B 1/273* (2006.01)
  *A61B 17/34* (2006.01)
  *A61B 17/22* (2006.01)

(52) U.S. Cl.
  CPC ............ *A61B 5/073* (2013.01); *A61B 17/3468* (2013.01); *A61M 25/0105* (2013.01); *A61B 1/00147* (2013.01); *A61B 1/041* (2013.01); *A61B 2017/22035* (2013.01); *A61B 1/273* (2013.01)
  USPC ............................ 600/114; 600/104; 600/112

(58) Field of Classification Search
  USPC ......... 600/104, 114, 127, 129, 175, 106, 113; 606/1; 604/891.1
  See application file for complete search history.

(56) References Cited

U.S. PATENT DOCUMENTS

3,757,781 A * 9/1973 Smart .............................. 604/59
3,934,584 A * 1/1976 Corio .............................. 604/59

(Continued)

FOREIGN PATENT DOCUMENTS

JP    5023322    2/1993
JP    6510936    12/1994

(Continued)

OTHER PUBLICATIONS

The International Search Report and Written Opinion of International Application No. PCT/US05/18290, mailed Jan. 17, 2008.

(Continued)

*Primary Examiner* — Alireza Nia
(74) *Attorney, Agent, or Firm* — Calfee, Halter & Griswold LLP

(57) ABSTRACT

A device for delivering an apparatus or object to a targeted location within a human subject is disclosed. The device includes a body, a handle mounted to and movable relative to the body, a tube, a cable, and retention unit. The tube has a first end fixed to the body and a second end fixed to the retention unit. The cable has a first end fixed to the handle and a second end remote from the body. The cable extends substantially through the tube. The retention unit applies a retention force sufficient to retain the capsule during endoscopic delivery to the targeted release location. Manipulation of the handle in a direction relative to the retention unit generates a force on the apparatus greater than the retention force. A method of use is also disclosed.

19 Claims, 7 Drawing Sheets

(56) References Cited

U.S. PATENT DOCUMENTS

| | | | |
|---|---|---|---|
| 4,198,960 A | | 4/1980 | Utsugi |
| 4,936,823 A | * | 6/1990 | Colvin et al. ................. 600/7 |
| 4,979,496 A | * | 12/1990 | Komi ........................ 600/113 |
| 5,259,366 A | * | 11/1993 | Reydel et al. ............. 600/124 |
| 5,312,415 A | | 5/1994 | Palermo |
| 5,350,397 A | | 9/1994 | Palermo et al. |
| 5,584,805 A | * | 12/1996 | Sutton ....................... 604/60 |
| 5,604,531 A | | 2/1997 | Iddan et al. |
| 5,653,677 A | | 8/1997 | Okada et al. |
| 5,681,279 A | * | 10/1997 | Roper et al. ............... 604/57 |
| 5,693,083 A | | 12/1997 | Baker |
| 5,785,685 A | * | 7/1998 | Kugler et al. ............ 604/99.03 |
| 6,071,279 A | * | 6/2000 | Whayne et al. ............ 606/41 |
| 6,123,683 A | * | 9/2000 | Propp ........................ 604/60 |
| 6,432,075 B1 | * | 8/2002 | Wada et al. ................. 604/15 |
| 6,632,171 B2 | | 10/2003 | Iddan et al. |
| 6,689,056 B1 | * | 2/2004 | Kilcoyne et al. .......... 600/300 |
| 6,884,213 B2 | * | 4/2005 | Raz et al. .................. 600/104 |
| 6,916,286 B2 | * | 7/2005 | Kazakevich ............... 600/173 |
| 6,960,183 B2 | * | 11/2005 | Nicolette .................... 604/57 |
| 6,984,205 B2 | * | 1/2006 | Gazdzinski ................ 600/160 |
| 7,001,329 B2 | * | 2/2006 | Kobayashi et al. ......... 600/114 |
| 7,020,531 B1 | * | 3/2006 | Colliou et al. ............. 607/133 |
| 7,104,968 B2 | * | 9/2006 | Swick ........................ 604/57 |
| 7,442,166 B2 | * | 10/2008 | Huang et al. .............. 600/160 |
| 2002/0103417 A1 | | 8/2002 | Gazdzinski |
| 2003/0013938 A1 | * | 1/2003 | Iddan et al. ................ 600/129 |
| 2003/0114776 A1 | * | 6/2003 | Griffin et al. .............. 600/585 |
| 2003/0120130 A1 | | 6/2003 | Glukhovsky et al. |
| 2003/0139647 A1 | | 7/2003 | Raz et al. |
| 2004/0006362 A1 | * | 1/2004 | Schaefer et al. ............ 606/200 |
| 2004/0111020 A1 | | 6/2004 | Long et al. |
| 2004/0153025 A1 | * | 8/2004 | Seifert et al. ................ 604/19 |
| 2005/0033319 A1 | * | 2/2005 | Gambale et al. ............ 606/139 |
| 2005/0222537 A1 | * | 10/2005 | Dinsmoor et al. ........... 604/174 |
| 2005/0245788 A1 | * | 11/2005 | Gerber ....................... 600/115 |
| 2008/0015413 A1 | * | 1/2008 | Barlow et al. .............. 600/114 |

FOREIGN PATENT DOCUMENTS

| | | |
|---|---|---|
| WO | 00/59376 A1 | 10/2000 |
| WO | 02/094092 | 11/2002 |

OTHER PUBLICATIONS

International Preliminary Report on Patentability from International Application No. PCT/US05/18290, mailed Mar. 3, 2009.

Carey, E.J. et al., Endoscopic capsule endoscope delivery for patients with dysphagia, anatomical abnormalities, or gastroparesis; Gastrointestinal Endoscopy, vol. 59, No. 2, 2004, pp. 423-426.

Supplementary Partial European Search Report from EP application No. EP 05 75 6202, completed Nov. 11, 2010, 4 pages.

* cited by examiner

DELIVERY DEVICE

CROSS-REFERENCE TO RELATED APPLICATIONS

This non-provisional application claims the benefit of U.S. Provisional Patent Application No. 60/574,070, entitled "Delivery Device," filed May 25, 2004, which is hereby incorporated in its entirety.

FIELD OF THE INVENTION

The present invention relates to a delivery device and more particularly to a delivery device for delivering an apparatus or object to an identified location within a human subject.

BACKGROUND OF THE INVENTION

The use of an endoscope to visualize a location within the human body is known in the art. As part of a medical procedure, a physician may wish to access the identified location with one or more tools, objects, or apparatus. Reaching the identified location with the apparatus may be difficult with the endoscope for many reasons, such as for example, the apparatus is larger than the diameter of the endoscope instrument channel diameter. One such apparatus is a image capturing device.

Several autonomous capsule devices are known in the art for capturing images within a human subject. These capsules typically contain a small power source and photographic capabilities for capturing images of the intestinal tract. One type of capsule known in the art is described in U.S. Pat. No. 5,604,531. For exemplary purposes, a typical capsule is about the size of a large vitamin.

After swallowing, the capsule passes through the gastrointestinal tract transmitting images to a recorder mounted in a belt-like device worn by the subject. One model of this capsule captures an image every 0.5 seconds. The images can be reviewed at a later date. One such capsule is the PILLCAM™ marketed by Givens Imaging Ltd.

A percentage of patients have difficulty swallowing the capsule, or in some cases, have a delayed entry into the small intestines, rendering the capsule powerless or with substantially reduced battery life prior to passing through some or all targeted areas to be photographed. Because this technique is often used for patients who present with difficult to diagnose symptoms, a complete set of images is important. Patients may have difficulty passing the capsule for many reasons, including oropharyngeal or mechanical dysphagia, gastroparesis and known or suspected anatomical abnormalities.

To solve these and other problems, the present invention can be used to deliver the capsule directly to a targeted location, either in the stomach or post-pylorically in the small intestine. The present invention uses a design having capsule retention and capsule expulsion features that are combined to create an inexpensive, reliable and easy to use product. Consequently, it is believed that a higher percentage of autonomous capsule devices will yield satisfactory results when delivered by the apparatus and method of the present invention. Further, the present invention is applicable to other monitoring devices, as well as other types of deliverable objects. Use of the device will reduce wasted video capsules, allow the esophagus to be traversed in patients that cannot swallow the capsule, and significantly increase the likelihood of complete image capture of the small intestines.

SUMMARY OF THE INVENTION

A device for delivering an image capturing capsule to a targeted release location within a human subject is disclosed. The device offers a physician increased confidence in the outcome of the procedure by overcoming patient inherent issues that prevent a complete image capture of the small intestines. It should be understood by others with ordinary skill in the art that the present invention has many applications beyond capsule delivery, and that capsule delivery is discussed for exemplary purposes only. The invention can be used to deliver any apparatus to a location with the body. After delivery the object can be released into the body, attached to another apparatus, or otherwise manipulated in a variety of ways.

The device includes a body, a handle mounted to and movable relative to the body, a tube, a cable extending through the tube, and a retention unit. The tube has a first end fixed to the body and a second end connected to the retention unit. The cable has a first end fixed to the handle and a second end remote from said body. The retention unit is sized to retain the capsule and applies a retention force sufficient to retain the capsule during endoscopic delivery to the targeted release location. Manipulation of the handle in a manner that directs the cable toward the retention unit generates a force on the capsule greater than the retention force, resulting in expulsion of the capsule from the retention unit.

Further features and advantages of the invention will become apparent from the following detailed description made with reference to the accompanying drawings.

The Detailed Description of the Invention merely describes preferred embodiments of the invention and is not intended to limit the scope of the claims in any way. Indeed, the invention as described by the claims is broader than and unlimited by the preferred embodiments, and the terms in the claims have their full ordinary meaning.

DESCRIPTION OF THE INVENTION

A device for delivering an apparatus or object to a targeted location within a subject is disclosed. The device may be used for any medical procedure that requires endoscopic or non-endoscopic delivery of a capsule, device, apparatus or object to a location within the human body. The device features a reliable structure and is constructed of relatively inexpensive materials.

Figure 1:
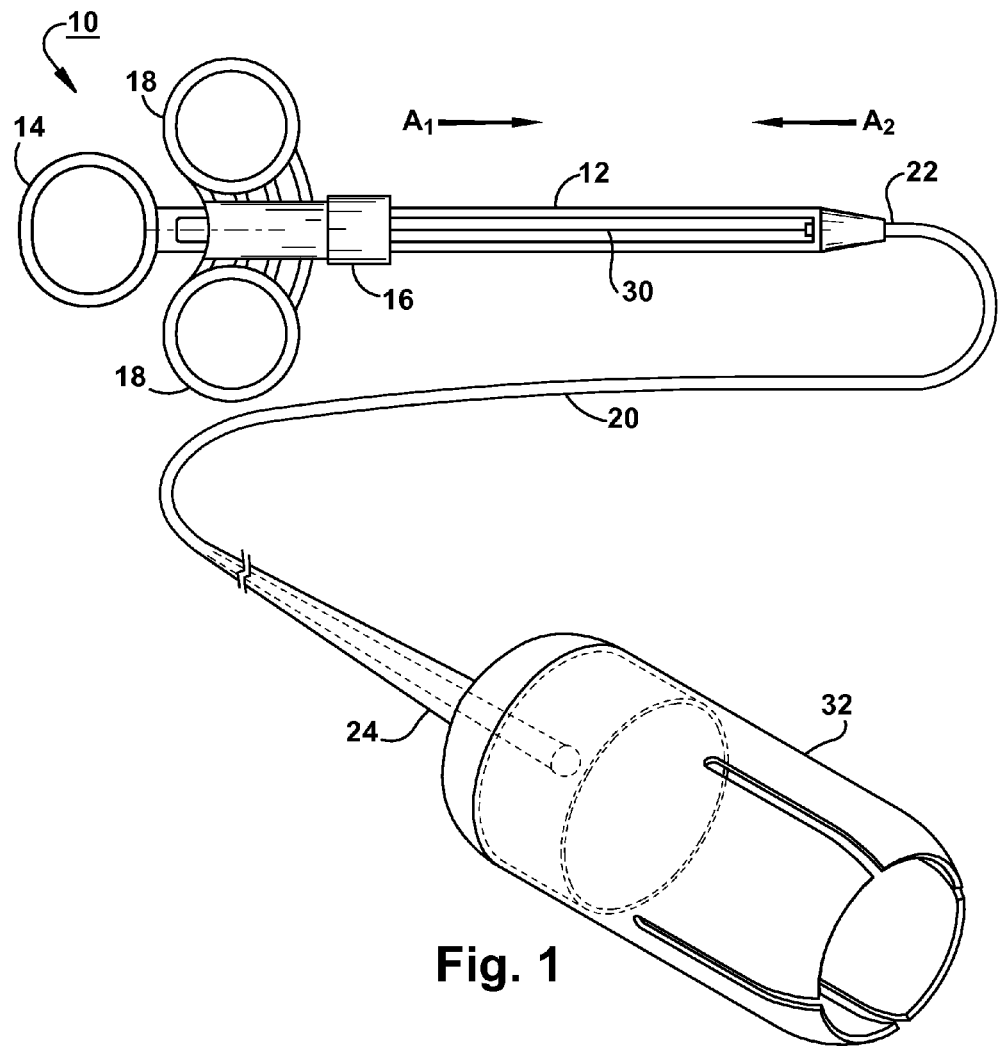
FIG. 1 is a perspective view of a capsule delivery device constructed in accordance with an embodiment of the present invention, showing a mechanical cup retention unit.

Referring now to the Figures, a perspective view of a capsule delivery device 10 constructed in accordance with an embodiment of the present invention is illustrated in FIG. 1. Any description of this device and all embodiments of the invention that use the terms proximal and distal are in relation to the physician, nurse, or technician operating the device.

The device 10 includes an elongated body 12 having a thumb ring 14 at a proximal end. A handle 16 is formed on the body 12 as separate piece. The handle is slidable relative to the body in the direction $A_1$, or an opposing direction $A_2$, by manipulation of two finger rings 18. The base 12 and handle 16 are formed of a rigid plastic material, although any suitable material may be used in the practice of the present invention.

A flexible tube 20 has a passage leading from a proximal end 22 to a distal end 24. The proximal end 22 of the tube 20 is fixed to the body 12. Any suitable known connection method or structure can be used. The tube can be constructed from any flexible durable material such as polyethylene.

The device 10 includes a cable 30 that extends substantially through the tube passage. The cable 30 has a proximal end fixed to the handle. The distal end of the cable 30 is connected to a retention unit 32, to be discussed later in greater detail. In this embodiment, the connection of the retention unit 32 to the cable 30 is made in part by a barb 34.

Figure 2:
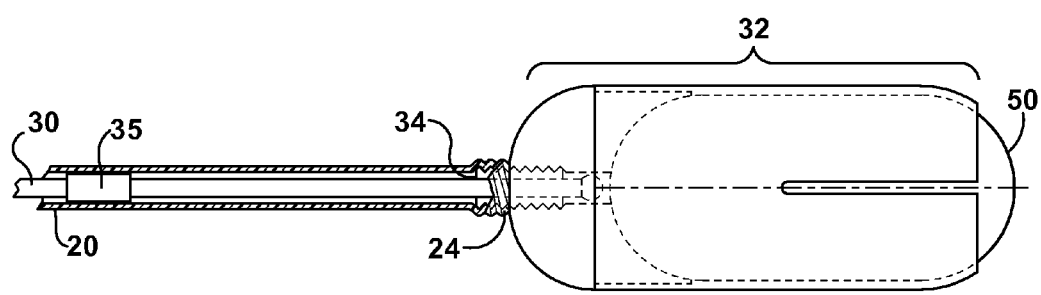
FIG. 2 is a side view of the mechanical cup retention unit illustrated in FIG. 1, showing a capsule loaded in the cup and detail of the cable and cup base structure.

FIG. 2 is a side view of the retention unit 32 illustrated in FIG. 1 with a capsule 50 loaded in the unit. As seen in FIG. 2, a shoulder stop 35 is fixed to the cable 30. When the handle is manipulated toward the retention unit, the shoulder stop 35 will impact the barb 34 and inhibit further movement of the cable 30 in the direction of the retention unit 32. The length from the stop 35 to the retention unit may vary in the practice of the present invention. However, the length is generally short enough to prohibit travel of the distal end of the cable 30 dangerously beyond the distal end of the retention unit 32.

Figure 16A:
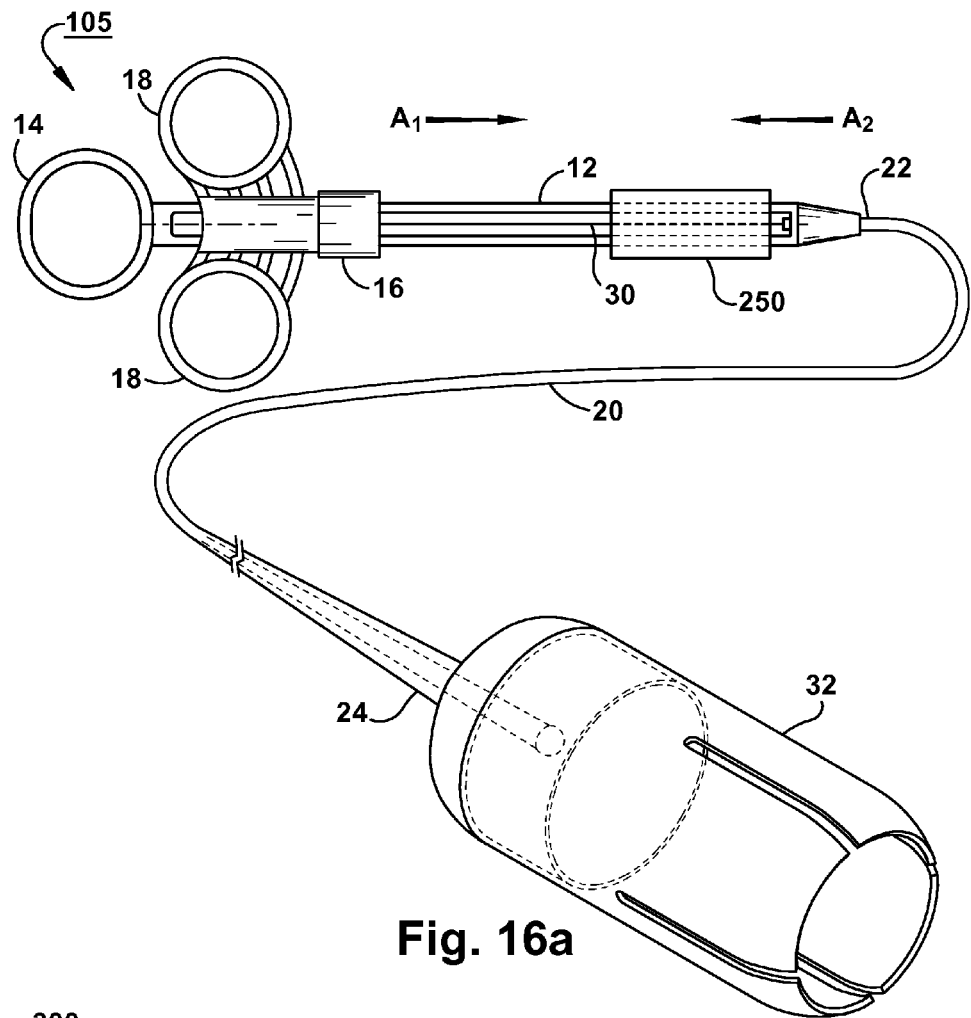
FIG. 16a is a perspective view of a capsule delivery device constructed in accordance with an embodiment of the present invention, showing a device with a proximal handle stop.

An alternative stop mechanism is shown in FIG. 16a. The device 105 includes a handle having a proximal handle stop 250 that limits the travel of the cable 30 in the distal direction $A_1$.

As discussed, the distal end of the cable 30 is connected to a barb 34 having a hollow interior and a threaded outer surface. The distal end 24 of the tube 20 is heat shrunk over the threads of the barb 34. The cable 30 is inserted through the hollow interior of the barb 34, and is disposed within a proximal portion of the retention unit 32. The distal end of the cable 30 includes a welded ball tip 36. The ball is sized to prevent the unit 32 from falling into the patient if the connection between the tube and the cup would fail.

Figure 3:
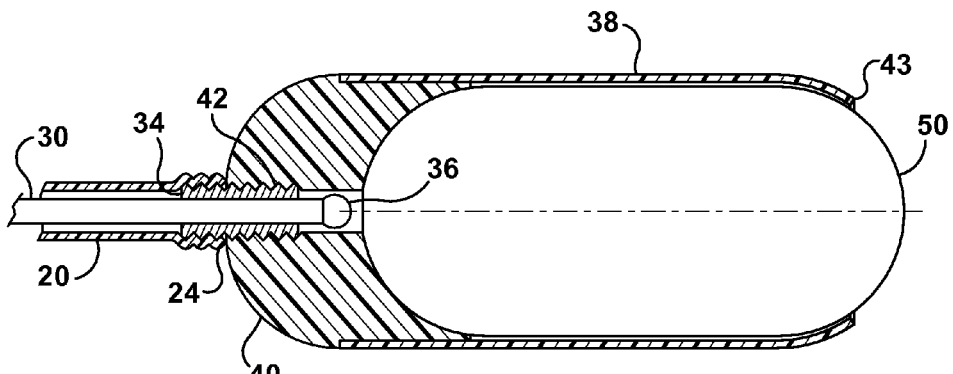
FIG. 3 is a side view, partially in section, of the mechanical cup retention unit illustrated in FIG. 1.

Referring now to FIG. 3, a side view, partially in section, of the retention unit 32 illustrated in FIGS. 1 and 2 is shown. The retention unit 32 is formed by joining a cylindrical shaped shell 38 on a light transmitting base 40. The shell 38 can be formed of a shape retaining plastic. The clear base 40 permits a physician to visually confirm expulsion of the capsule 50 at the end of the procedure. The base 40 further includes a threaded aperture 42 for connection to the barb 34. As a result, the base 40 is fixed relative to the tube 20 and the body 12.

As shown in FIG. 3, the retention unit is holding a capsule 50. The shell 38 is sized to retain the capsule 50 and includes a contoured distal end leading to an opening 43. This opening allows an operator to load the capsule 50 into the unit 32 by manually pressing the capsule through the opening 43 toward the base 40. After the capsule is press fit into the position shown in FIG. 3, frictional retention forces emitted by the shell 38 upon the capsule 50 are sufficient to retain the capsule within the shell 38 during the endoscopic delivery process.

In practice of the invention, tube is inserted through the endoscope instrument channel. The barb may be covered with a protector to limit damage to the channel. After the barb is beyond the distal end of the endoscope, the protector is removed and the base 40 is threaded onto the barb 34. Next, the capsule 50 is loaded into the unit 32 with the base 40 threaded on the barb 34. The patient is then intubated to a targeted release point. A physician uses the optical features of the endoscope to determine the targeted release point. As discussed, this point in different patients will vary, depending upon their own need for delivery by this device 10. Once at or adjacent the targeted release point, the physician will expel the capsule 50.

Figure 4:
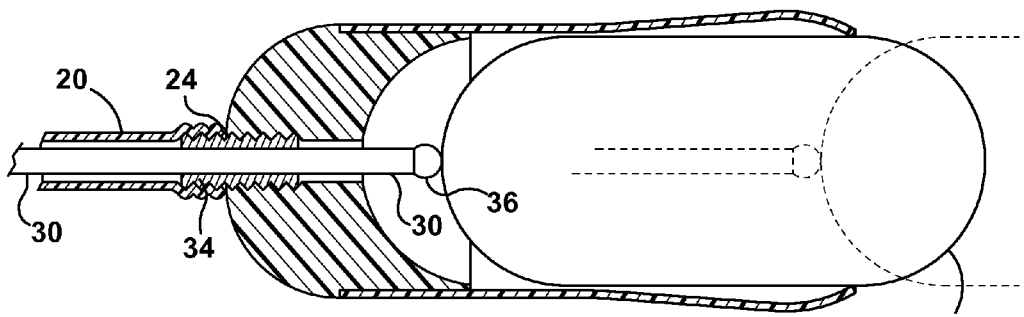
FIG. 4 is a side view, partially in section, of the mechanical cup retention unit illustrated in FIG. 1, showing a capsule being expelled from the cup.

FIG. 4 is a side view, partially in section, of the mechanical cup 32 illustrated in FIGS. 1-3, showing a capsule being expelled. When an operator is ready to expel the capsule, the ring handle 18 is manipulated by the operator to create axial movement of a cable 30 toward the capsule 50. The cable 30 contacts the capsule and applies sufficient force to expel the capsule from the shell 38. The cable 30 in a post-expulsion position is shown in phantom lines. Alternatively to a cable, it should be understood by others with ordinary skill in the art that the present invention may be practiced with a wire, a tube or any elongated member of sufficient strength and support to expel the capsule. It is believed capsule expulsion yields better results than any passive release technique.

Figure 5:
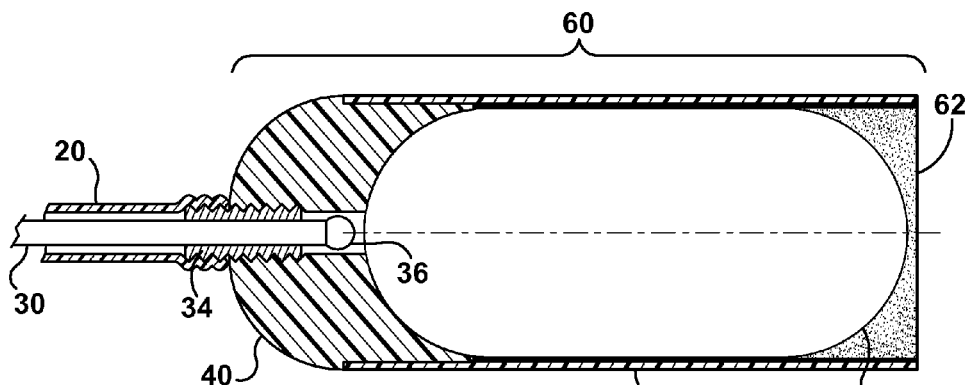
FIG. 5 is a side view, partially in section, of a portion of a capsule delivery device constructed in accordance with another embodiment of the present invention, showing a viscous fluid-filled retention unit.

Another embodiment of the present invention is shown in FIG. 5. The cup unit 60 holds a capsule 50 and contains a highly viscous material 62 at its distal end. The combined frictional retention forces emitted by the shell 61 and the material 62 upon the capsule are sufficient to retain the capsule within the shell during the delivery process. The expulsion mechanism is the same as previously described.

Figure 6:
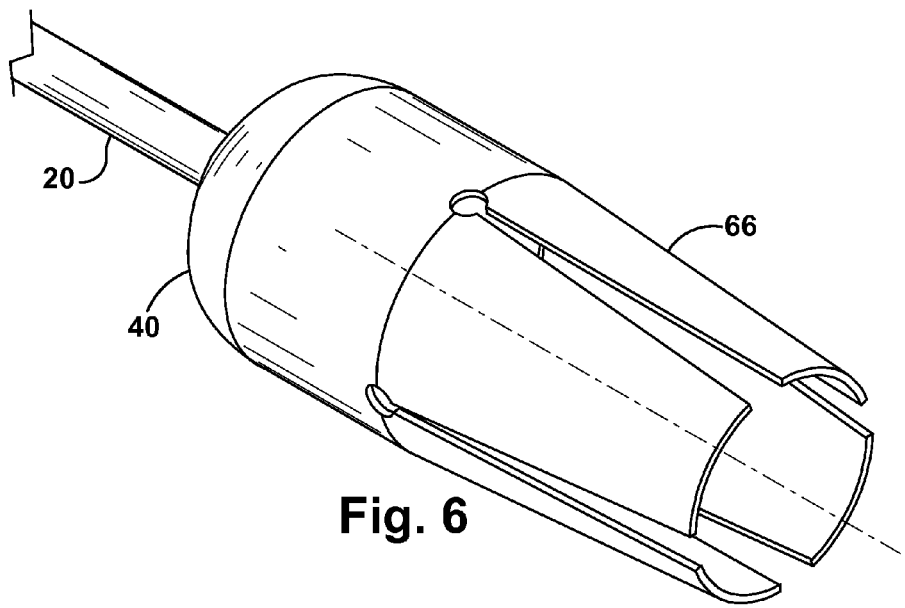
FIG. 6 is a perspective view of a portion of a capsule delivery constructed in accordance with yet another embodiment of the present invention, showing a slotted mechanical cup retention unit.
Figure 7:
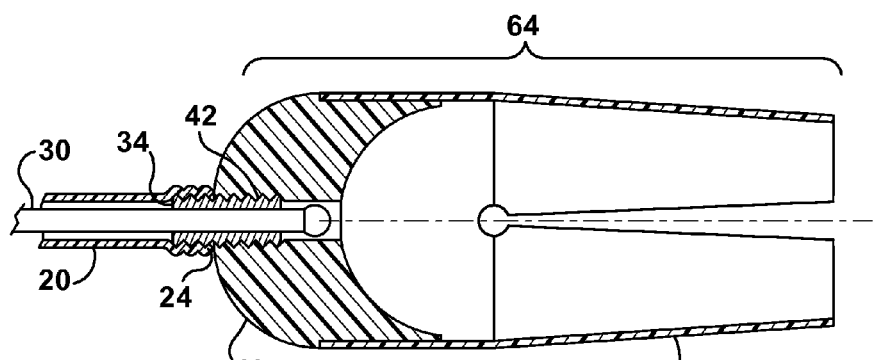
FIG. 7 is a side view, partially in section, of the mechanical cup retention unit illustrated in FIG. 6.

FIGS. 6 and 7 shown yet another embodiment of the present invention. FIG. 6 is a perspective view of a retention unit 64 constructed of a clear base 40 and a slotted shell 66. The shell 66 is molded with an inward bias toward its distal end. The frictional retention forces emitted by the shell 66 are sufficient to retain the capsule within the shell 66 during the delivery process. The loading process and expulsion process used in the operation of this embodiment are the same as previously described.

Figure 8:
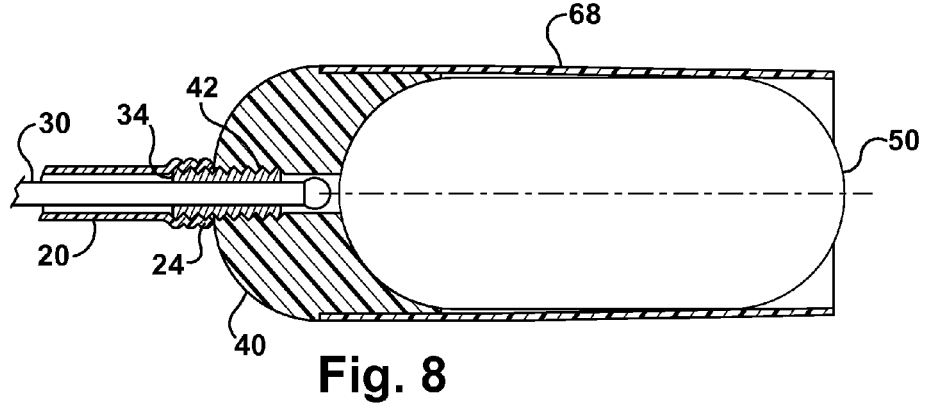
FIG. 8 is a side view, partially in section, of a portion of a capsule delivery device constructed in accordance with yet another embodiment of the present invention, showing an elastameric cup retention unit.

In a yet another embodiment, FIG. 8 illustrates a retention unit that includes a clear base 40 and a capsule cup 68. The capsule cup 68 is cooperatively shaped and slightly undersized in relation to the capsule 50. The capsule cup 68 is constructed of an elastomeric material such as silicon. After manual insertion that stretches the cup, the capsule is held tight within the capsule cup 68 by frictional forces. These forces upon the capsule are sufficient to retain the capsule within the cup 68 during endoscopic delivery of the capsule. The capsule is expelled from the cup 68 by manipulation of the cable 30 as in the previous embodiments.

Figure 9:
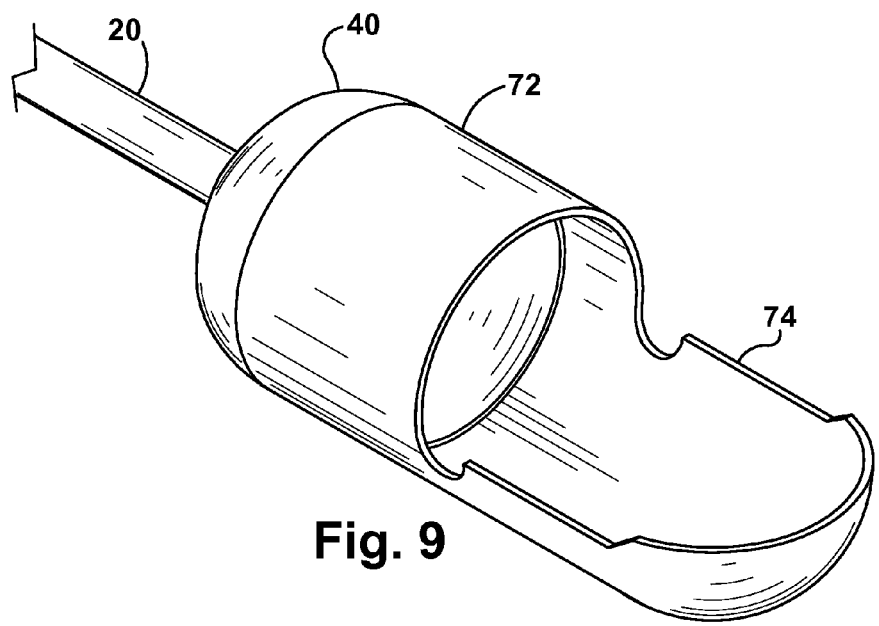
FIG. 9 is a perspective view of a portion of a capsule delivery constructed in accordance with yet another embodiment of the present invention, showing a mechanical cup retention unit with a semi-circumferential expulsion orifice.
Figure 10:
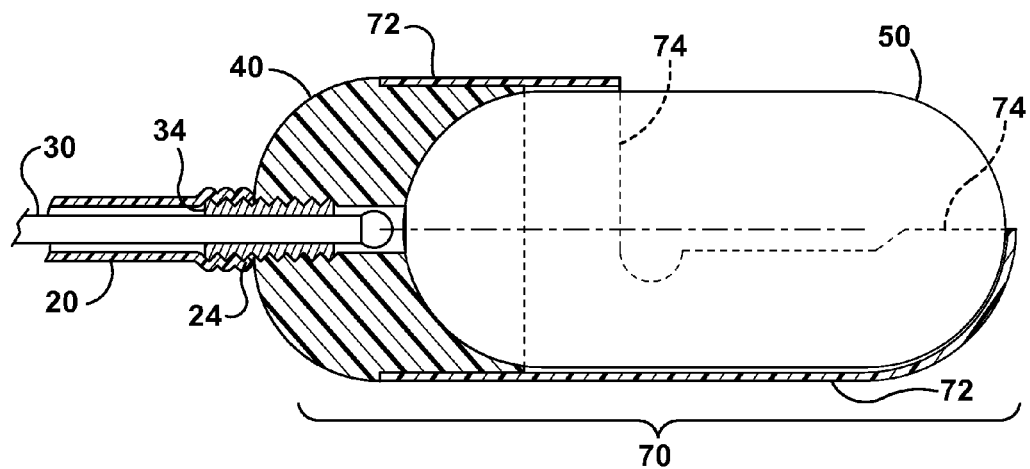
FIG. 10 is a side view, partially in section, of the mechanical cup retention unit illustrated in FIG. 9, showing a capsule loaded into the cup.

Referring now to FIG. 9, a perspective view of a retention unit 70 of yet another embodiment of the present invention is illustrated. FIG. 10 is a side view, partially in section, of the retention unit 70 showing a loaded capsule 50. The unit 70 includes a clear base 40 and a molded shell 72. The shell in constructed with an irregular-shaped, semi-circumferential orifice 74 at its distal end, through which the capsule 50 will be expelled.

Figure 11:
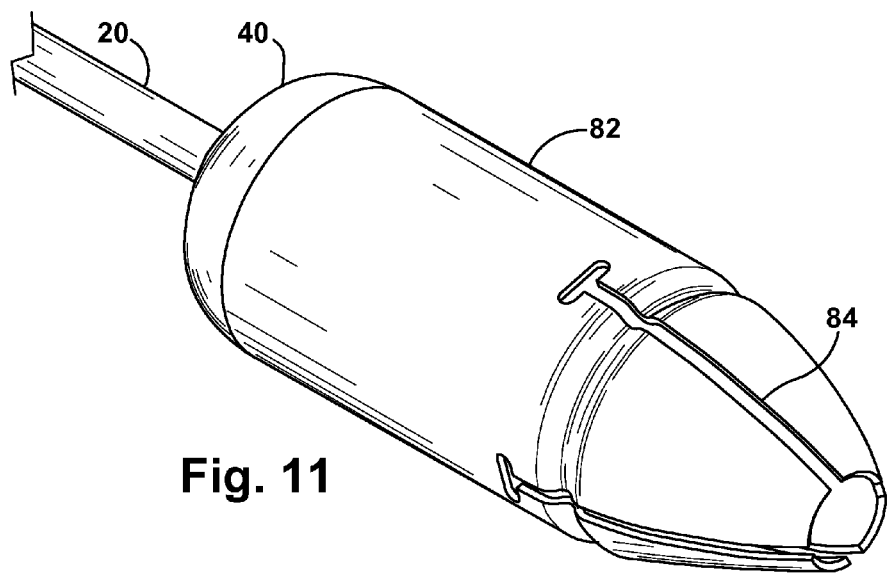
FIG. 11 is a perspective view of a portion of a capsule delivery constructed in accordance with yet another embodiment of the present invention, showing a mechanical cup retention unit with a slotted and tapered distal end.
Figure 12:
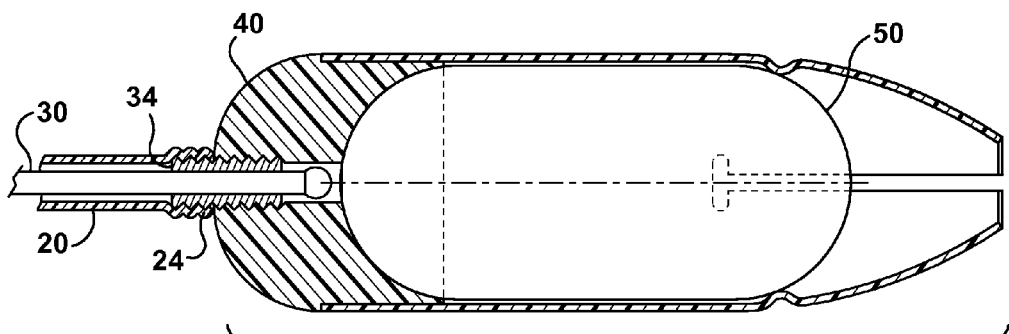
FIG. 12 is a side view, partially in section, of the mechanical cup retention unit illustrated in FIG. 11, showing a capsule loaded into the cup.

FIGS. 11 and 12 shown yet another embodiment of the present invention. The retention unit 80 illustrated includes a clear base 40 and a shell 82. FIG. 12 is a side view, partially in section, of the retention unit 80 showing a loaded capsule 50. The shell is generally bullet shaped and has a tapered distal end. The tapered shape is believed to reduce friction when the endoscope is being intubated to the targeted release point. The distal end further includes a series of slots 84 that allow the distal end opening to expand during loading of the capsule 50.

Figure 13:
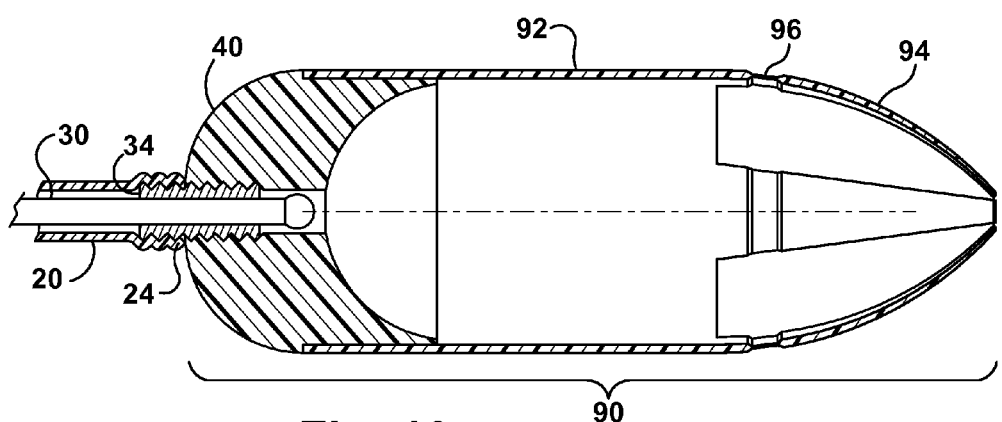
FIG. 13 is a side view of a portion of a capsule delivery constructed in accordance with yet another embodiment of the present invention, showing a mechanical cup retention unit with a hinged distal end.

Referring now to FIG. 13, a side view of a portion of a capsule delivery constructed in accordance with yet another embodiment is shown. The retention unit 90 includes a clear base 40 and a hinged shell 92. A series of swinging members 94 extend toward the distal end of the shell 92. The members 94 are movable about a series of machined or molded hinges 96. The loading process and expulsion process used in the operation of this embodiment are the same as previously described.

Figure 14:
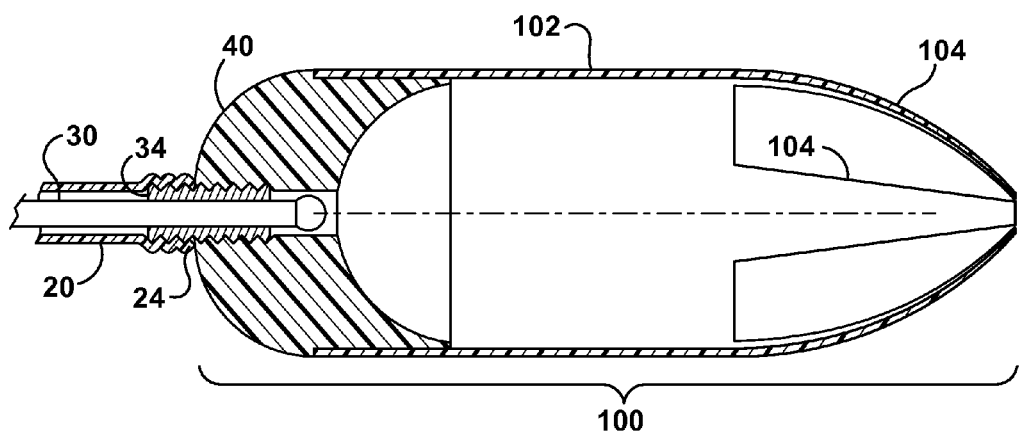
FIG. 14 is a side view of a portion of a capsule delivery constructed in accordance with yet another embodiment of the present invention, showing a mechanical cup retention unit having a distal end with extending tongues.

Yet another embodiment of the present invention is shown in FIG. 14. The retention unit 100 includes a clear base 40 and a shell 102. A plurality of tongues 104 extend from the distal end of the shell 102. The tongues are flexible to allow loading and expulsion of a capsule (not shown).

Figure 15:
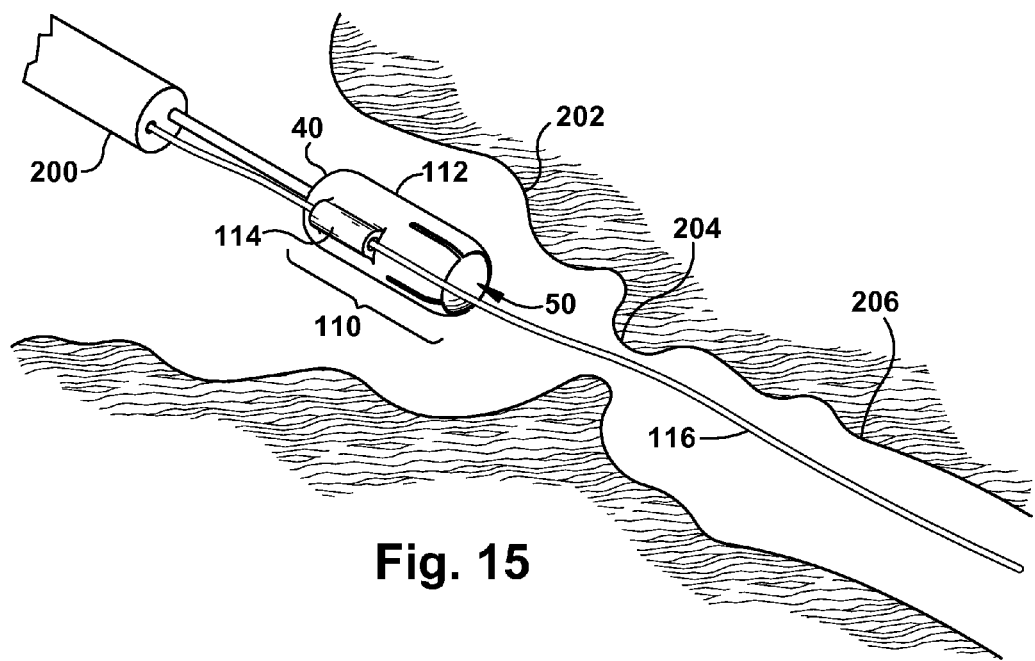
FIG. 15 is a perspective view of a portion of a capsule delivery constructed in accordance with yet another embodiment of the present invention, showing a mechanical cup retention unit having a guide wire channel.

FIG. 15 is a perspective view of yet another embodiment of the present invention. The device is shown in use during an endoscopic procedure. As shown, an endoscope 200 has been intubated into the stomach 202 of a patient. The procedure illustrated in FIG. 15 is intended to release the capsule 50 beyond the pyloric sphincter 204 into the duodenum 206, i.e., the first portion of the small intestines. If the capsule 50 is expelled into the small intestines at the beginning of image transmission, the odds of recording the entire targeted field before expiration of the battery are increased.

The retention unit 110 shown has a clear base 40 and a shell 112 that includes a channel 114. A guide wire 116 has been threaded through the channel of a dual channel gastroscope 200. The guide wire 116 is beneficial in traversing the pyloric sphincter 204. Alternatively, the guide wire 116 may be inserted by a single channel standard gastroscope. In this procedure, the scope is then backed out, the capsule is loaded at the distal end of the scope, and the guide wire is inserted in the side channel 114 of the shell. Then, the patient in intubated again. Still another alternative technique is the use of a therapeutic gastroscope having a channel large enough for the guide wire 116 and the tube 20 to be threaded together.

Figure 16B:
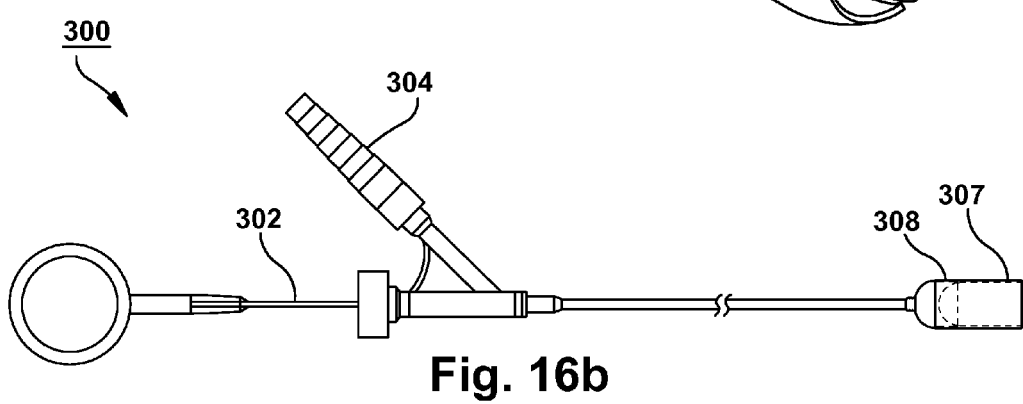
FIG. 16b is a perspective view of a portion of a capsule delivery constructed in accordance with yet another embodiment of the present invention, showing a suction retention unit.

It should be understood by other with ordinary skill in the art that a wide variety of other retention unit structures can be used in the practice of the present invention. For example, the capsule may be retained in the retention unit by vacuum forces. Such a device 300 is shown in FIG. 16b. The device 300 includes a capsule cup 307 and a vacuum cup 308 co-axially disposed therein. The capsule cup 307 is cooperatively shaped and oversized in relation to the capsule (not shown). The vacuum cup 308 inner surface is sized to engage an end portion of the capsule along a center axis thereof. The capsule is held tight within the vacuum cup 308 by suction forces.

As shown, the vacuum cup 308 is in fluid communication with a suction supply (not shown) applied at an inlet port within the step adapter 304. The suction forces upon the capsule are sufficient to retain the capsule within the cups 307, 308 during endoscopic delivery of the capsule. When an operator is ready to expel the capsule, the suction forces are removed. Next, the capsule is expelled from the cups 307, 308 by manipulation of the cable 302

While several embodiments of the invention has been illustrated and described in considerable detail, the present invention is not to be considered limited to the precise constructions disclosed. Various adaptations, modifications and uses of the invention may occur to those skilled in the arts to which the invention relates. It is the intention to cover all such adaptations, modifications and uses falling within the scope or spirit of the annexed claims.

What is claimed is:

1. A device having a portion insertable into an instrument channel of an endoscopy for delivering an object to a targeted release location within a human subject, the object enveloped by a smooth rounded exterior surface, the device comprising:
   a. a body having a first passage therethrough;
   b. a flexible elongated tube having a first end proximal with and fixed to said body and a second end distal from said body, said tube configured for insertion into the instrument channel of the endoscope and defining a second passage aligned with said first passage;
   c. a solid cable having a first end and a second end and slidably engaged within said first passage and said second passage concurrently;
   d. a handle fixed to said cable first end and movable relative to said body; and
   e. a cylindrical-shaped retention unit having a dome-shaped proximal end removably connected to said tube second end and a distal end defining an opening smaller than a diameter of the object, wherein said unit applies a mechanical retention force to at least a portion of a distal end of the smooth rounded exterior surface of the object sufficient to retain the object during delivery to said targeted release location when said flexible elongated tube and said retention unit extends distally from the instrument channel of the endoscope;
   f. wherein manipulation of said handle in a direction relative to said retention unit creates distal movement of said cable, whereby said cable second end is extendable beyond said tube second end to generate sufficient force against at least a portion of the smooth rounded exterior surface of the object to expel the object from said retention unit, and to the targeted release location when said flexible elongated tube and said retention unit extends distally from the instrument channel of the endoscope.

2. The device of claim 1 wherein said retention unit comprises a shell sized to hold said object therein.

3. The device of claim 1 wherein said retention unit comprises a shell having an outer surface defining an opening sized to allow a manual press fit of said object therethrough.

4. The device of claim 1 wherein said retention unit comprises a cup having a suction port in communication with a suction source.

5. The device of claim 1 wherein said object is an image capturing capsule.

6. The device of claim 1 wherein said body comprising a handle stop, wherein said handle stop limits axial travel of said cable in a distal direction.

7. A device having a portion insertable into an instrument channel of an endoscopy for delivering an image capturing capsule to a targeted release location within a human subject, the image capturing capsule having a uniform smooth exterior surface, and the device comprising:
   a. a body;
   b. a handle mounted to and movable relative to said body;
   c. a flexible tube having a first end fixed to said body and a second end, said tube defining a passage and opening at said second end with said tube sized for insertion into the instrument channel of the endoscope;
   d. a solid cable having a first end fixed to said handle and a second end flexibly remote from said body, said cable extending substantially through said tube passage; and
   e. a cylindrical-shaped retention unit having a dome-shaped proximal end removably connected to said tube second end and a distal end defining an expandable opening smaller than a widthwise diameter of the capsule, wherein said unit is sized to contact and surround at least a portion of a distal end of the capsule and applies a retention force on the uniform smooth exterior surface of the distal end of the capsule sufficient to retain the capsule during endoscopic delivery to said targeted release location;
   f. wherein manipulation of said handle in a direction relative to said retention unit generates a force on the uniform smooth exterior surface of the capsule greater than said retention force to project the capsule from the retention unit.

8. The device of claim 7 wherein said retention unit comprises a clear base and a cylindrical shaped shell having an open distal end.

9. The device of claim 7 wherein said retention unit comprises a shell having a distal end opening of sufficient size to allow a manual press fit of said capsule therethrough.

10. The device of claim 7 wherein said retention unit comprises a shell having a plurality of longitudinal slots.

11. The device of claim 7 wherein said cable comprises a stop member to limit movement of the cable second end in a direction toward said retention unit.

12. The device of claim 7 wherein said cable second end comprises a ball-shaped tip.

13. The device of claim 7 wherein said retention unit comprises a shell having an exterior surface channel through which a guide wire may be threaded.

14. The device of claim 7 wherein said body comprising a handle stop, wherein said handle stop limits axial travel of said cable in a distal direction.

15. The device of claim 7 wherein said retention unit comprises a cup having a suction port in communication with a suction source.

16. A device for delivery of an object to within a subject, the device comprising:
   a body;
   a handle slidable relative to the body;
   a tube having a proximal end fixed to the body and a distal end;
   a barb connected to the distal end of the tube;
   a retention unit having a proximal end connected to the barb and a distal end defining an opening, the retention unit defining an expandable chamber, the expandable chamber moveable between a closed position and an expanded position for allowing a manual press fit of the object therethrough the distal end opening, wherein a diameter of the distal end opening in the closed position is less than a maximum outer diameter of the object and a length of the expendable chamber is longer than a length of a constant diameter portion of the object; and
   a cable having a proximal end fixed to the handle and a distal end, the cable extending inside the retention unit.

17. The device of claim 16 wherein the distal end of the cable is a ball tip, wherein the ball tip prohibits the retention unit from disconnecting from the cable if the barb disconnects from the tube.

18. The device of claim 16 wherein the distal end of the barb forms a threaded connection to the retention unit and the distal end of the tube is heat shrunk to the proximal end of the barb.

19. The device of claim 16 wherein manipulation of the handle in a direction relative to the retention unit creates distal movement of the cable, whereby the cable distal end generates sufficient force against the object to expel the object from the retention unit in the distal direction and out the distal end opening.

* * * * *